United States Patent [19]

Traas

[11] 4,152,355
[45] May 1, 1979

[54] PROCESS FOR THE PREPARATION OF BOLL WEEVIL SEX PHEROMONE COMPONENTS

[75] Inventor: Petrus C. Traas, Naarden, Netherlands

[73] Assignee: Naarden International N.V., Naarden-Bussum, Netherlands

[21] Appl. No.: 765,382

[22] Filed: Feb. 3, 1977

[30] Foreign Application Priority Data

Feb. 4, 1976 [GB] United Kingdom ............... 4416/76

[51] Int. Cl.$^2$ .......................................... C07C 45/00
[52] U.S. Cl. ................................. 260/598; 568/591; 260/340.9 R; 568/828
[58] Field of Search ....................................... 260/598

[56] References Cited

FOREIGN PATENT DOCUMENTS 2152193 4/1973 Fed. Rep. of Germany.

OTHER PUBLICATIONS

Minkin et al., Russian Chemical Reviews (Uspekhi Khimii), vol. 29, No. 11 (1960), pp. 599–617.
Olah et al., Friedel Crafts & Related Reaction, (III) Part 2 (1964), 1225–1240.

Primary Examiner—Bernard Helfin
Attorney, Agent, or Firm—Kane, Dalsimer, Kane, Sullivan and Kurucz

[57] ABSTRACT

A new intermediate of formula I

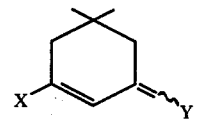

in which X is chlorine, bromine or hydrogen and Y is a free or protected —CHO group, which is used in the manufacture of boll weevil sex pheromone components of formula II

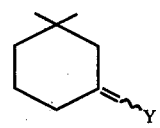

in which Z is —CHO or —CH$_2$OH, by catalytic hydrogenation, optionally with protection of the formyl group of II by acetalisation. Compound II is prepared by formylation of isophorone directly or after reduction and dehydration.

3 Claims, 1 Drawing Figure

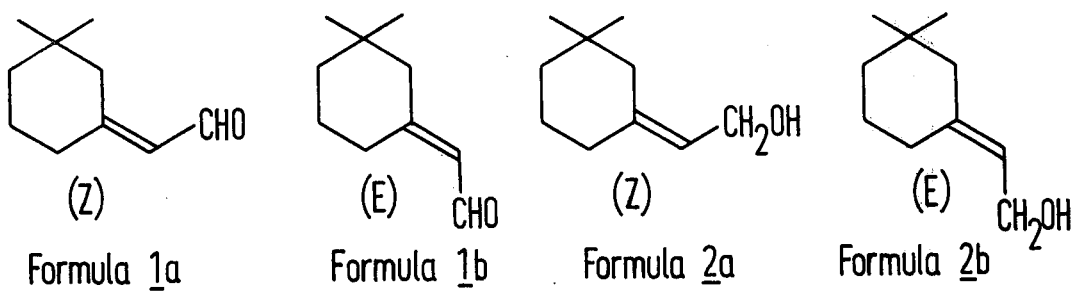
Formula 1a  Formula 1b  Formula 2a  Formula 2b
Reaction Scheme A
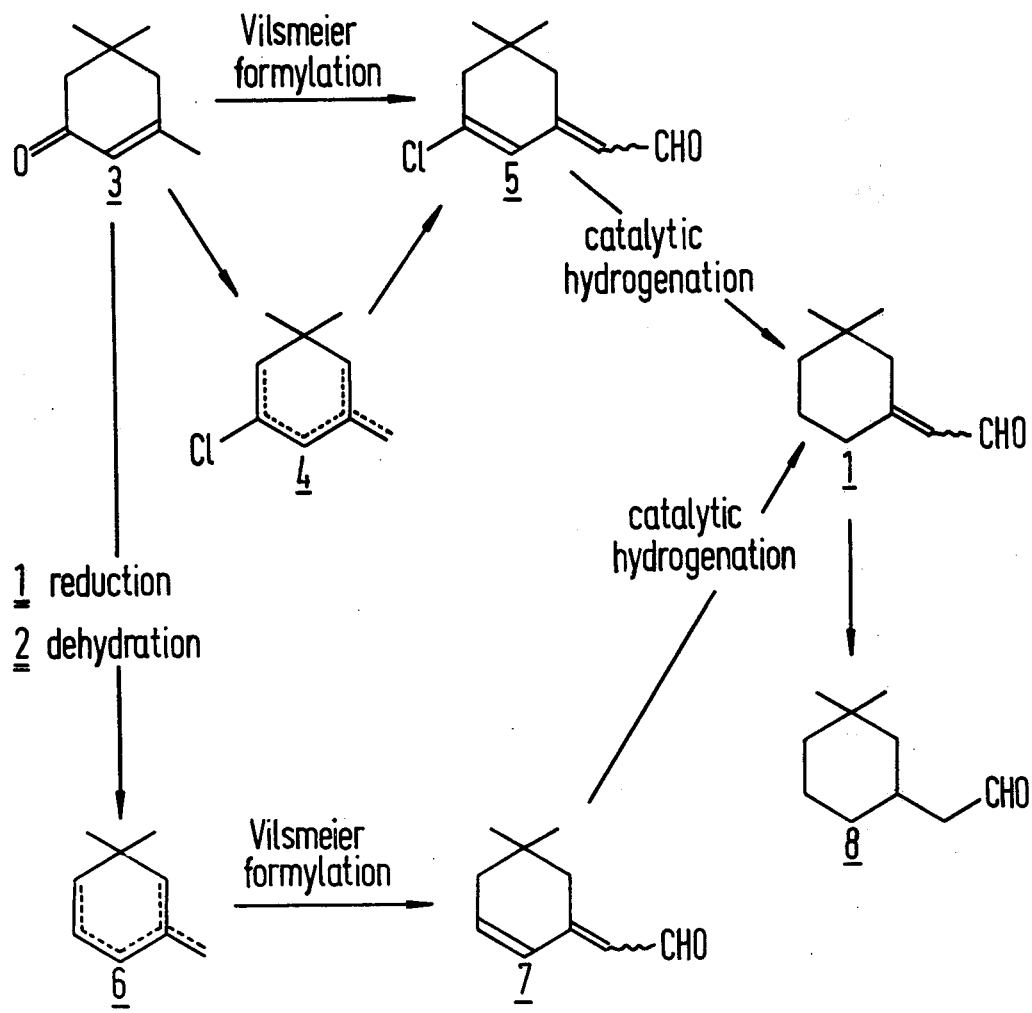

Reaction Scheme B
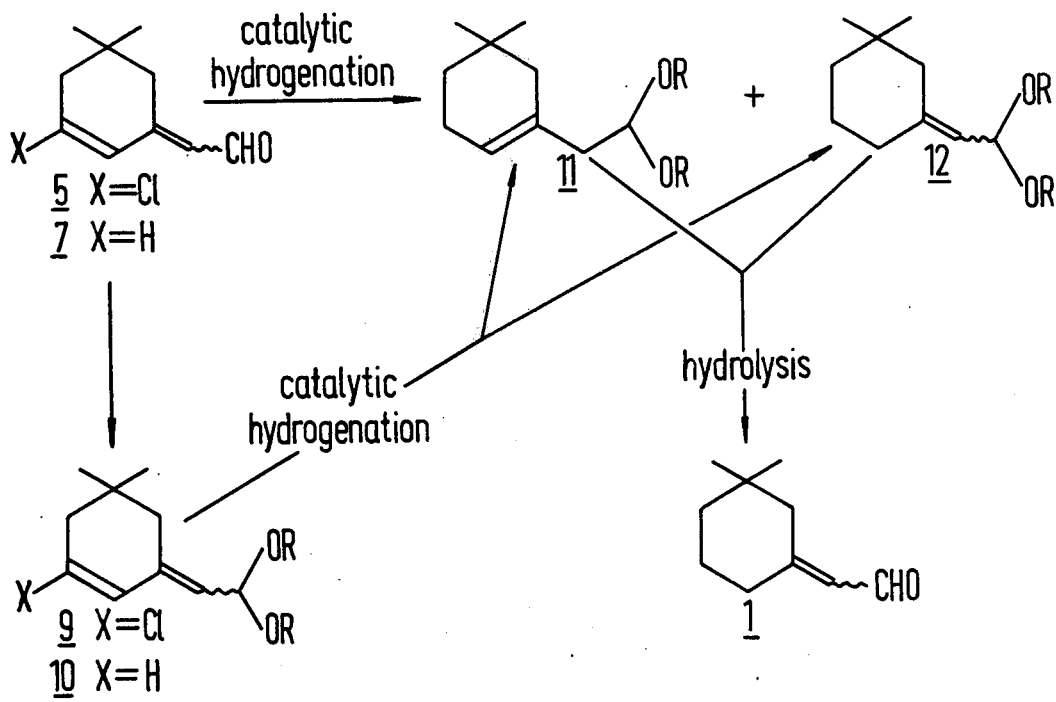
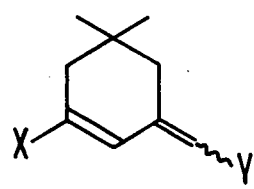
Formula I
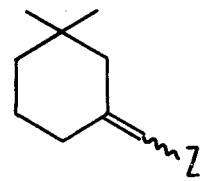
Formula II

PROCESS FOR THE PREPARATION OF BOLL WEEVIL SEX PHEROMONE COMPONENTS

BACKGROUND OF THE INVENTION

1. Field of the Invention

This invention relates to a synthesis of some components of the Boll Weevil sex attractant. More particularly this invention relates to a novel synthesis of the compounds 1a and b and 2a and b (numbers refer to the formulae shown on the accompanying drawings).

2. Brief Description of the Prior Art

The compounds 1a and b and 2a are known to be components of the sex pheromone of the male Boll Weevil (Anthonomus Grandis). The sex pheromone can play a prominent part in selective and relatively low toxic ways of fighting this noxious insect. It is therefore important that the components of the sex pheromone are easily accessible. The compounds 1a and b and 2a have been prepared in several ways. However either difficultly accessible and expensive starting materials had to be used, or many and/or difficult reaction steps had to be carried out. The majority of the known synthesis routes starts with 3,3-dimethylcyclohexanone. The first reaction step may be:

a. A Reformatsky-type reaction with zinc and ethyl bromo-acetate. see: J. H. Tumlinson et al., J. Org. Chem. 36 (1971), p. 2617 and U.S. Pat. Nos. 3,813,443 and 3,895,078.

b. A Wittig-type reaction. see: O. P. Vig et al., J. Indian Chem. Soc. 49 (1972), p. 1181.

c. A Wittig-type reaction (Horner modification), see: J. H. Babler and T. R. Mortell, Tetrahedron Letters 1972, p. 669.

d. A condensation reaction with acetylene, see: C. A. Vodoz and H. Schinz, Helv. Chim. Acta 33 (1950), p. 1321.

In British Pat. No. 1,341,015 a synthesis route is described wherein addition of HCl to myrcene at $-50°$ C. is used as the first reaction step.

Isophorone is a cheap and abundantly available material. Formylation of isophorone (compound 3) on its single methyl group would provide a compound with the carbon skeleton of aldehyde 1 (a and/or b) although in a different oxidation state. However, formylation of unsaturated ketones is limited to a very few examples and is known to produce almost exclusively polyformylated products. (see e.g. V. M. Vlasov and O. V. Zakharova, Zh. Org. Khim. 10 (1974), p. 66 cf. Chem. Abstracts 80 (1974), 108113e; Z. Arnold and A. Holy, Coll. Czech. Chem. Comm. 30 (1965), p. 47; A. Holy and Z. Arnold, Coll. Czech. Chem. Comm. 30 (1965), p. 53.)

It was now found that compounds 1a and b may be easily obtained from isophorone applying as the essential reaction steps a formylation reaction, preferably a Vilsmeier formylation reaction, and a catalytic hydrogenation, as outlined in reaction schemes A and B, shown in the accompanying drawings.

Vilsmeier reactions are described, for example, by G. A. Olah and S. J. Kuhn in "Friedel-Crafts and Related Reactions" edited by G. A. Olah, 3, Part 2, p. 1211, Interscience Publishers (1964), G. Hazebroucq, Annales Pharmaceutiques Francaises, 24, (1966) p. 793; V. I. Minkin and G. N. Dorofeenko, Russian Chem. Review (Uspekhi Khimi) 29 (1960) p. 599.

DETAILED DESCRIPTION OF THE INVENTION

The formylation of isophorone, leading to the chlorohexenylidene-acetaldehyde 5 is carried out using a formamide and a Lewis acid in a suitable solvent at a temperature between $0°$ and $150°$ C.

Suitable formamides are, for example, dimethylformamide, dimethyl thioformamide and methyl-phenylformamide. Dimethylformamide is preferred.

Suitable Lewis acids are, for example, phosphorus oxychloride, phosgene, thionylchloride, oxalylchloride, ethyl chloroformate and their bromine analogues. Phosphorus oxychloride ($POCl_3$) and phosgene ($COCl_2$) are preferred. The reaction is advantageously carried out at a temperature of from $20°$ to $100°$ C. and preferably from $50°$ to $90°$ C. The solvent should be aprotic and inert, e.g. benzene, cyclohexane or trichloro-ethylene. The reaction may, however, be carried out in an excess of dimethylformamide. Under the conditions of the formylation reaction a small amount of a mixture of bromo- or chlorodienes with the structure of formula 4 (see reaction scheme A) may be formed intermediately, especially in an inert solvent, thereby consuming some of the Lewis acid. In these solvents it is therefore advantageous to use a small excess of Lewis acid. The compounds 4 smoothly react further giving the bromo- or chlorocyclohexenylidene-acetaldehyde 5.

Alternatively isophorone may first be reduced with the aid of a complex metal hydride to the corresponding alcohol and subsequently dehydrated in a known way, e.g. with $H_2SO_4$ or $Al_2O_3$, yielding the mixture of dienes of formula 6. This mixture of dienes can be formylated in a Vilsmeier-type reaction completely analogous to the formylation of isophorone, yielding cyclohexenylidene-acetaldehyde 7.

The compounds 5 and 7 can be converted into the mixture of cyclohexylidene-acetaldehydes 1 in substantially the same way. The key step is a catalytic hydrogenation, reducing a doubly unsaturated aldehyde to a mono-unsaturated aldehyde. The choice of the catalyst determines whether or not the aldehyde group must be protected, preferably by conversion into an acetal.

The aldehydes 5 and 7 may be reduced to the mixture of aldehydes 1 using a Raney nickel catalyst. If an alcohol is used as the solvent enough base should be present to prevent acetal formation. However a complicated reaction mixture is obtained, containing apart from the desired aldehyde 1 also the starting material, much of the completely saturated aldehyde 8 and even the corresponding completely saturated alcohol.

Therefore, the preferred process of reducing the aldehydes 5 and 7 directly to the mixture of aldehydes 1 uses a moderated or partially poisoned catalyst selected from the group consisting of palladium, rhodium, ruthenium and platinum catalysts.

Palladium on charcoal, moderated or poisoned e.g. with sulfur and quinoline is highly preferred, but Lindlar catalyst, or Lindlar catalyst additionally poisoned with sulfur and/or quinoline is also very suitable. This reduction reaction may be carried out at temperatures above or below room temperature. At elevated temperatures the reduction proceeds fast but produces a considerable amount of the completely saturated aldehyde 8 (reaction scheme A). When the reduction is carried out at or below room temperature the alpha,beta-unsaturated aldehyde 1 is obtained in high yield and only a minor amount (less than 10%) of 8 is present.

The reduction may be carried out in any solvent suitable for use in catalytic hydrogenations; an alcohol, for example, methanol or ethanol, may be advantageously used. To prevent acetal formation in these solvents, it is advantageous to keep the reaction mixture slightly alkaline. In the case of reduction of the bromo- or chloro-aldehyde 5 this requires at least one equivalent of a suitable base (e.g. an alkali metal hydroxide or a lower tertiary amine), to neutralize the hydrogen chloride formed during this reduction.

Alternatively, the aldehydes 5 and 7 may be reduced to the aldehyde 1 with a Raney nickel catalyst after the aldehyde group has been protected. This may be done either separately before the reduction or, in the case of acetalisation, in situ during the reduction (reaction scheme B).

Acetalisation is the preferred method of protection, and may be carried out in any known manner, for example, by reaction with an alcohol, a diol, or an epoxide, for example, ethylene oxide.

Separate acetalisation of 5 and 7 with an epoxide, alcohol or diol, e.g. ethylene glycol, in acidic medium leads to the compounds 9 and 10 respectively. These compounds can be reduced with a Raney nickel catalyst in an alkaline medium to a mixture of the mono-unsaturated acetals 11 and 12. On reduction of 9 sufficient base must be added to trap the liberated hydrogen chloride or hydrogen bromide. A low molecular weight organic base, for example, triethylamine is suitable.

The compounds 5 and 7 may also be reduced directly to a mixture of 11 and 12 using Raney nickel catalyst in an alcoholic solvent in the presence of a small amount of acid. In this case the acetals 9 and 10 are formed in situ during the reduction. Starting with compound 5, enough hydrogen bromide or chloride is produced to make the medium acidic, but with compound 7 it is advantageous to add a small amount of a mineral acid.

On careful hydrolysis of the mixture of acetals 11 and 12 with oxalic acid in aqueous acetone only 12 is converted to the corresponding aldehyde 1 (mixture of Z and E isomers). On acid hydrolysis under more drastic conditions, compound 11 is both hydrolysed and isomerized and thus also yields aldehyde 1.

The Vilsmeier formylation reaction of isophorone produces a mixture of Z and E isomers of aldehyde 5.

The isomer ratio in this mixture if retained during the further reaction sequence and is therefore also found in aldehyde 1.

The ratio of the amounts of the Z(1a) and E(1b) isomers of aldehyde 1 depends on the reaction conditions chosen and will generally be between 3:1 and 1:3.

The mixture of stereoisomeric aldehydes 1 as obtained from the reaction may be isomerised to approximately a 1:1 ratio by treatment with p-toluene sulphonic acid in a carbon tetrachloride solution.

Both isomeric aldehydes may be reduced to the corresponding alcohols (2a and b) by standard reduction techniques, e.g. with sodium borohydride or another complex metal hydride. The aldehyde and alcohol isomers may be isolated from their respective isomer mixtures by standard separation techniques, e.g. fractional distillation, or G.L.C.

The following Examples illustrate the invention.

EXAMPLE 1

Synthesis of chloro-cyclohexenylidene-acetaldehyde 5

Phosphorus oxychloride (307 g.; 2 moles) was added to a stirred solution of dimethylformamide (182.5 g.; 2.5 moles) in benzene (400 ml.) at 10°–20° C. over a period of 45 minutes. After additional stirring at room temperature for 15 minutes, isophorone (138 g.; 1 mole) was added dropwise at reflux temperature. After the addition was complete, the reaction mixture was refluxed for 2 hours. The mixture was subsequently cooled, poured into a cold aqueous solution of sodium acetate and stirred for 15 minutes. The organic layer was separated and the aqueous layer extracted with benzene (200 ml.) The combined organic layers were washed with water and dried over MgSO$_4$. Solid sodium acetate (10 g.) was added to the benzene solution. The solvent was evaporated and the residue was distilled (over NaOAc) to give 148.0 g. (80%) of compound 5, b.p. 105°–110° C./1 Torr.

The formylation of isophorone was also performed in dimethylformamide as the solvent, giving a 50% yield of compound 5.

EXAMPLE 2.

Direct reduction of compound 5 to cyclohexylidene-acetaldehyde 1.

A solution of compound 5 (3.7 g.; 20 mmole) and triethylamine (4 g.; 40 mmole) in methanol (59 ml.) was hydrogenated at 0° C. over a palladium on charcoal catalyst poisoned with sulfur and quinoline (e.g. of Johnson Matthey Chemicals Limited of 74 Hatton Garden, Londen E.C.1).

After 2.05 equivalents of hydrogen were consumed (0.05 equivalent excess is needed to ensure reduction of all starting material), the reduction was stopped and the catalyst was filtered off. The solvent was evaporated and the resulting suspension was triturated 3 times with 20 ml. pentane. The pentane solution was distilled to give 3.7 g. (100%) of the compound 1 as a mixture of Z and E stereoisomers (contaminated with 5% of the completely saturated compound 8). B.p. 83°–85° C./4 Torr.

EXAMPLE 3.

Synthesis of cyclohexenylidene-acetaldehyde 7

Isophorone (138 g.; 1 mole) was added to a solution of sodium dihydrobis(2-methoxy-ethoxy)aluminate (202 g.; 1 mole) in ether (300 ml.). After the addition was complete, the reaction mixture was refluxed for ½ hour, cooled, poured onto ice and filtered through Celite. The organic layer was separated and the aqueous layer was extracted with ether (150 ml.). The combined organic layers were washed and dried over MgSO$_4$. After evaporation of the solvent the residue was distilled to afford 125.8 g. (89%) of 3,5,5-trimethyl-cyclohex-2-enol. Distillation of this compound through a column packed with Al$_2$O$_3$ and heated to 300° C., afforded in 90% yield the mixture of dienes 6, b.p. 50°–52° C./45 Torr.

The formylation of these dienes to cyclohexenylidene-acetaldehyde 7 proceeded completely analogous to example 1.

EXAMPLE 4

Direct reduction of compound 7 to cyclohexylidene-acetaldehyde 1

A solution of compound 7 (3.0 g.; 20 mmole) and triethylamine (0.4 g.) in methanol (50 ml.) was hydrogenated at 0° C. over a palladium on charcoal catalyst poisoned with sulfur and quinoline. After 1.05 equivalent of hydrogen was consumed, the reduction was stopped and the catalyst was filtered off. The solvent was evaporated and the residue distilled under reduced pressure to yield 2.9 g. (95%) of the compound 1 as a mixture of Z and E isomers (contaminated with 6% of the completely saturated product 8). B.p. 83°–84° C./4 Torr.

EXAMPLE 5

Conversion of cyclohexenylidene-acetaldehydes 5 and 7 to acetals 9 and 10

Compound 5 (36.9 g.; 0.2 mole) was azeotropically acetalized with glycol (18.6 g.; 0.3 mole) in toluene (500 ml.) under the influence of a catalytic amount of p-toluene-sulfonic acid. After removal of the calculated amount of water, the acid was neutralised with solid sodium carbonate. The solvent was removed under reduced pressure and the residue was distilled to yield 41.2 g. (90%) of compound 9 (R+R=—CH$_2$CH$_2$—). B.p. 123°–127° C./1 Torr.

In exactly the same way cyclohexenylidene-acetaldehyde 7 was converted to acetal 10 (R+R=—CH$_2$CH$_2$—).

EXAMPLE 6

Reduction of acetals 9 and 10 to the mixture of acetals 11 and 12

A solution of glycol acetal 9 (45.7 g.; 0.2 mole) and triethylamine (30.3 g.; 0.3 mole) was hydrogenated at room temperature over Raney nickel in methanol (500 ml.) as the solvent. The reduction was stopped when 0.4 mole of hydrogen was consumed. The catalyst was filtered off and the solvent removed under reduced pressure. The resulting suspension was triturated with pentane (4×100 ml.). The pentane solution was distilled to give 39.2 g. (100%) of a mixture of 33% of glycol acetal 11 and 67% of glycol acetal 12 (R+R=—CH$_2$CH$_2$—). B.p. 83°–87° C./1 Torr. The glycol acetal 10 was reduced in substantially the same way as glycol acetal 9, yielding the same mixture of glycol acetals 11 and 12. Only 0.01 mole instead of 0.3 mole of triethylamine was added before reduction, and the reduction was stopped when 1 equivalent of hydrogen was consumed.

EXAMPLE 7

Hydrolysis of acetals 11 and 12 to cyclohexylidene-acetaldehyde 1

A mixture of the cyclohexylidene-acetaldehyde acetals 11 and 12 (R+R=—CH$_2$CH$_2$—or R=CH$_3$) (19.5 g.; 0.1 mole) dissolved in aqueous acetone (200 ml.) was stirred at room temperature with oxalic acid (1 g.) for 3 hours. The solution was extracted 3 times with ether. The combined ether layers were washed with water and dried over MgSO$_4$. After evaporation of the solvent the residue was chromatographed over silica gel. 9.1 g. of compound 1 and 6.0 g. of acetal 11 were obtained. Acetal 11 (6.0 g.) was dissolved in a mixture of acetic acid (50 ml.), water (10 ml.) and a catalytic amount of p-toluene-sulfonic acid and heated to 40° C. for 2 hours. The solution was diluted with water (200 ml.) and extracted 3 times with ether. The combined ether layers were washed with NaHCO$_3$ solution to neutral and dried over MgSO$_4$. After evaporation of the solvent the residue was distilled under reduced pressure, yielding 4.6 g. (95%) of compound 1 (mixture of Z and E isomers).

EXAMPLE 8

Reduction of cyclohexenylidene-acetaldehydes 5 and 7 to the mixture of acetals 11 and 12 and hydrolysis to aldehyde 1

A solution of compound 5 (36.9 g.; 0.2 mole) was hydrogenated at room temperature over Raney nickel in methanol as the solvent. The reduction was stopped when 0.4 mole of hydrogen was consumed. The catalyst was filtered off. Triethylamine was added (30.3 g.; 0.3 mole) and the solvent was subsequently removed under reduced pressure. The resulting suspension was triturated with pentane (4×100 ml.). The pentane solution was distilled to give 33.6 g. (85%) of a mixture consisting of 33% dimethylacetal 11 and 67% dimethylacetal 12 (R=CH$_3$). B.p. 64°–68° C./1 Torr. This mixture of acetals was hydrolysed to the aldehyde 1 with a mixture of acetic acid and water, according to the procedure of example 7.

Alternatively the catalyst was removed from the reaction mixture of the catalytic hydrogenation and the solvent subsequently evaporated. The residue was dissolved in a mixture of acetic acid (200 ml.), water (20 ml.) and a catalytic amount of p-toluenesulfonic acid and heated to 40° C. for 5 hours. The mixture was diluted with water (200 ml.), extracted with ether and the ether layer washed with NaHCO$_3$ solution to neutral and dried over MgSO$_4$. After evaporation of the solvent the residue was distilled under reduced pressure, yielding 35 g. (95%) of compounds 1 as a mixture of Z and E isomers.

In substantially the same way compound 7 was converted to compound 1. A drop of concentrated hydrochloric acid was added before reduction. The reduction was stopped when 1 equivalent of hydrogen was consumed.

EXAMPLE 9

Reduction of cyclohexylidene-acetaldehyde 1 to cyclohexylidene-ethanol 2

Compound 1 (15.2 g.; 0.1 mole) was added to a solution of sodium dihydrobis(2-methoxy-ethoxy) aluminate (20.2 g.; 0.1 mole) in ether (50 ml.). After the addition was complete the reaction mixture was refluxed for ½ hour, cooled, poured onto ice and filtered through Celite. The organic layer was separated and the aqueous layer was extracted with ether (30 ml.). The combined organic layers were washed and dried over MgSO$_4$. After evaporation of the solvent the residue was distilled to afford 14.6 g. (95%) of the cyclohexylidene-ethanol 2 as a mixture of its Z and E isomers.

I claim:

1. A process for preparing a compound of formula:

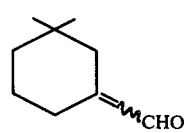

which comprises;
hydrogenating a compound of formula;

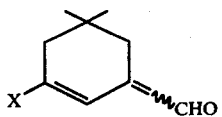

wherein X is selected from chlorine and bromine, in the presence of a catalyst selected from the group consisting of moderated palladium, partially poisoned palladium, rhodium, ruthenium and platinum.

2. The process of claim 1 wherein the catalyst is selected from the group consisting of moderated platinum on charcoal, palladium on charcoal poisoned with sulfur and quinoline, Lindlar catalyst, Lindlar catalyst poisoned with sulfur, Lindlar catalyst poisoned with quinoline, and Lindlar catalyst poisoned with sulfur and quinoline.

3. The process of claim 1 wherein hydrogenation is carried out at or below room temperature.

* * * * *